United States Patent
Eischeid

(10) Patent No.: US 9,210,954 B1
(45) Date of Patent: Dec. 15, 2015

(54) BIB FOR RELIEVING A FEVER

(71) Applicant: Jo Ann Eischeid, Roscoe, IL (US)

(72) Inventor: Jo Ann Eischeid, Roscoe, IL (US)

( * ) Notice: Subject to any disclaimer, the term of this patent is extended or adjusted under 35 U.S.C. 154(b) by 0 days.

(21) Appl. No.: 14/659,744

(22) Filed: Mar. 17, 2015

(51) Int. Cl.
*A41B 13/00* (2006.01)
*A41B 13/10* (2006.01)
*A61F 7/10* (2006.01)

(52) U.S. Cl.
CPC ............... *A41B 13/103* (2013.01); *A61F 7/10* (2013.01)

(58) Field of Classification Search
CPC ............... A61F 2007/0231; A61F 7/02
See application file for complete search history.

(56) References Cited

U.S. PATENT DOCUMENTS

| | | | |
|---|---|---|---|
| 2,697,424 A * | 12/1954 | Hanna | 607/114 |
| 4,845,788 A | 7/1989 | Meyer | |
| 4,924,528 A | 5/1990 | Trombetti-Dickens | |
| D357,568 S | 4/1995 | Schottland | |
| 5,509,141 A * | 4/1996 | Saltzman | 2/49.2 |
| 5,911,311 A | 6/1999 | Hutchins | |
| 6,327,712 B1 | 12/2001 | Armstrong | |
| 6,442,759 B1 | 9/2002 | Straham, Jr. | |
| 7,100,211 B2 * | 9/2006 | Bruffett | 2/49.2 |
| 2002/0052566 A1* | 5/2002 | Sequeira | 601/112 |
| 2002/0069446 A1 | 6/2002 | Pinckney | |
| 2011/0023761 A1 | 2/2011 | Ekelund | |

* cited by examiner

*Primary Examiner* — Anna Kinsaul

(57) ABSTRACT

The bib for relieving a fever is a child-care accessory adapted for us in caring for an infant or small child. The bib for relieving a fever is a bib that can be secured around the neck of a child or a caretaker. The bib contains a cold pack that) prevents heat transfer from the caretaker to the child when the child is being held, and helps to cool the child. The bib for relieving a fever includes a bib and a cold pack.

1 Claim, 4 Drawing Sheets

BIB FOR RELIEVING A FEVER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of child care accessories and medical devices, more specifically, a bib configured for use in child care.

SUMMARY OF INVENTION

The bib for relieving a fever is a child care accessory adapted for us in caring for an infant or small child. The bib for relieving a fever is a bib that can be secured around the neck of a child or a caretaker. The bib contains a cold pack that 1) prevents heat transfer from the caretaker to the child when the child is being held; and 2) helps to cool the child. The bib for relieving a fever comprises a bib and a cold pack.

These together with additional objects, features and advantages of the bib for relieving a fever will be readily apparent to those of ordinary skill in the art upon reading the following detailed description of the presently preferred, but nonetheless illustrative, embodiments when taken in conjunction with the accompanying drawings.

In this respect, before explaining the current embodiments of the bib for relieving a fever in detail, it is to be understood that the bib for relieving a fever is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the bib for relieving a fever.

It is therefore important that the claims be regarded as including such equivalent construction insofar as they do not depart from the spirit and scope of the bib for relieving a fever. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

Figure 1:
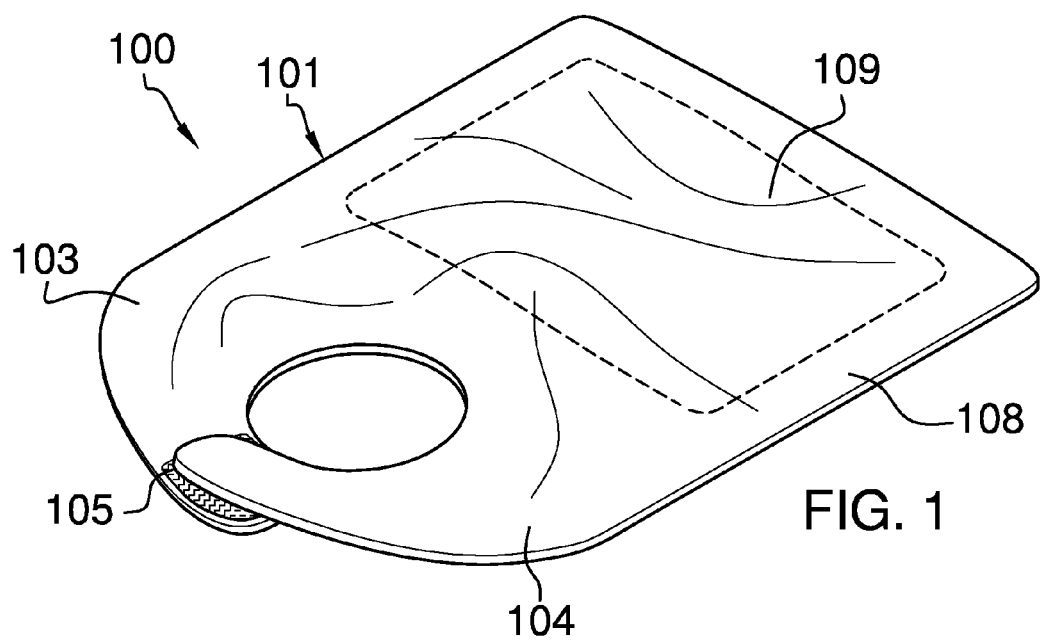
FIG. 1 is a perspective view of an embodiment of the disclosure.
Figure 2:
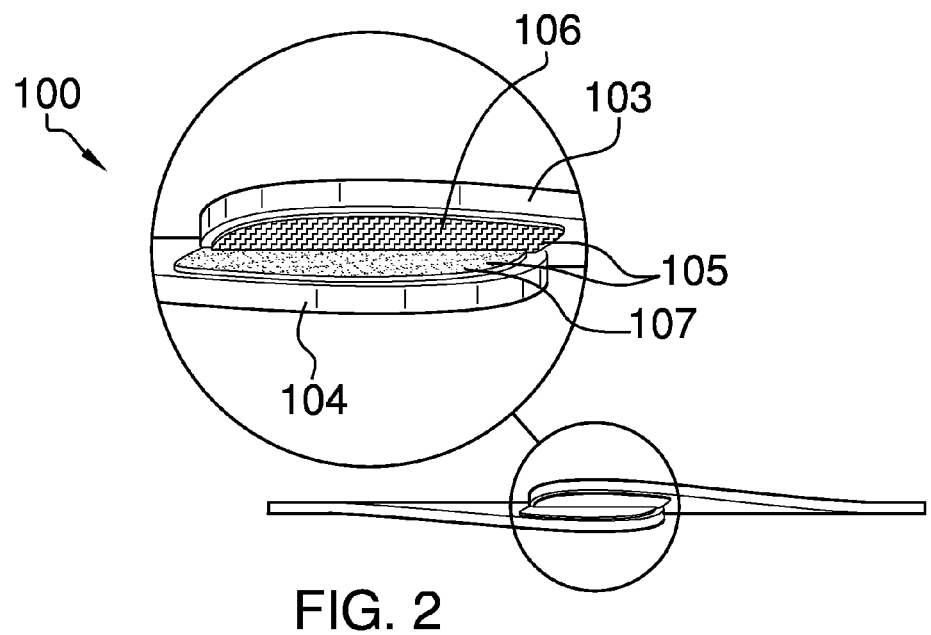
FIG. 2 is a detail view of an embodiment of the disclosure.
Figure 3:
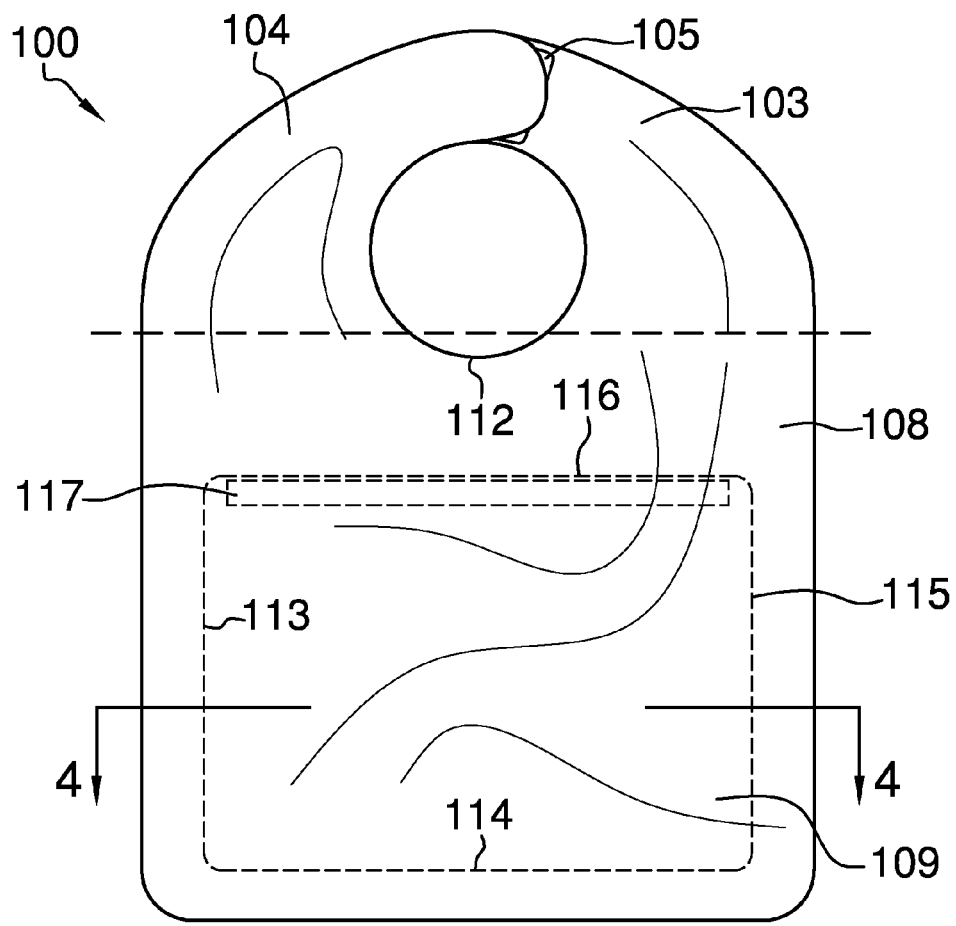
FIG. 3 is a front view of an embodiment of the disclosure.
Figure 4:
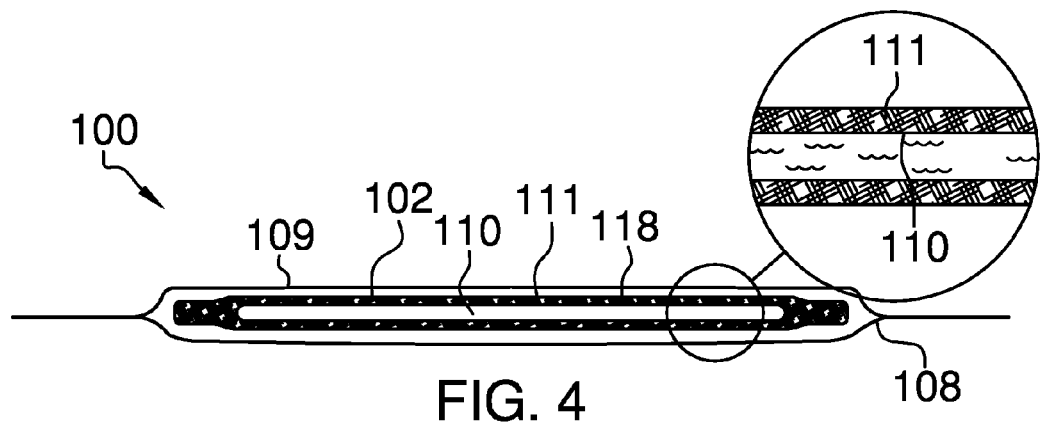
FIG. 4 is a cross-sectional view of an embodiment of the disclosure across line 4-4 in FIG. 3.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to a first potential embodiment of the disclosure, which is illustrated in FIGS. 1 through 6. The bib for relieving a fever 100 (hereinafter invention) comprises a bib 101 and a cold pack 102.

The bib 101 comprises a first strap 103, a second strap 104, a hook and loop fastener 105, a hook surface 106, a loop surface 107, a body 108, and a pocket 109. The body 108 is a roughly rectangular shaped textile or sheeting. The purpose of the body 108 is to protect the clothing of the caretaker 141 and the child 142. Attached to the body 108 is the first strap 103 and the second strap 104. The first strap 103 and the second strap 104 are formed from textile or sheeting. The first strap 103 and the second strap 104 are wrapped around the neck 143 of the wearer to secure the bib 101 in place. The first strap 103 and the second strap 104 are secured using the hook and loop fastener 105, which comprises a hook surface 106 and a loop surface 107. The hook surface 106 is attached to the first strap 103. The loop surface 107 is attached to the second strap 104. Optionally, the bib 101 can have a curved depression 112 formed in it between the first strap 103 and the second strap 104 to accommodate the neck 143 of the wearer.

The pocket 109 is a rectangular shaped textile or sheeting. The purpose of the pocket 109 is to create a pouch 118 within which the cold pack 102 can be placed. The pocket 109 further comprises a first edge 113, a second edge 114, a third edge 115 and a fourth edge 116. The first edge 113, second edge 114, and third edge 115 are attached to the body 108. Once the first edge 113, second edge 114, and third edge 115 are attached to the body 108 a pouch 118 is created into which the cold pack 102 is placed. Optionally, a closing device 117 can be used to secure the cold pack 102 within the pouch 118 by closing the fourth edge 116.

The cold pack 102 can be commercially purchased or custom made. If the cold pack 102 is custom made, the cold pack 102 further comprises an alcohol solution 110 and a sealed pouch 111. The alcohol solution 110 is a 30% (v/v) solution of 2-propanol in water. The alcohol solution 110 is stored in the sealed pouch 111, which is a commercially available vacuum seal pouch. The alcohol 110 solution is placed in the open vacuum seal pouch and the open vacuum seal pouch is then sealed to create the sealed pouch 111.

Textiles used in this disclosure may be made of natural or synthetic fibers including, but not limited to, cotton, nylon, and polyester. Sheeting used in this disclosure may be made of plastic including, but not limited to, polyethylene or polyurethane. Hook and loop fasteners are readily and commercially available.

The hook surface 106 and the loop surface 107 can be attached to the first strap 103 and the second strap 104 respectively by several methods including, but not limited to, sewing or glue. The first edge 113, second edge 114, and third edge 115 can be affixed to the body 108 using several methods including, but not limited to, sewing or glue. The optional closing devices 117 include, but are not limited to, the use of zippers, buttons, or hook and loop fasteners. Methods to attach closing devices to textiles and sheeting are well known and documented in the art. The body 108, can be formed as a single unit with the first strap 103 and the second strap 104.

Vacuum seal bags and 2-proponal are readily and commercially available. Alternatively, commercially available cold packs are readily available.

To use the invention 100, the cold pack 102 is placed in a freezer. Once the cold pack 102 is thoroughly chilled, the cold pack 102 is placed in the pocket 109. If the invention 100 is fitted with the optional closing device 117, the pocket 109 is closed. The invention 100 is secured by bringing the first strap 103 and the second strap 104 around the neck 143 of the caretaker 141 and then pressing the hook surface 106 on the first strap 103 against the loop surface 107 on the second strap 104. By holding the child 142 against the pocket 109, the caretaker 141 can care for the child 142 while the cold pack 102 prevents the transfer of body heat from the caretaker 141 to the child 142 (see FIG. 6). To remove the invention 100, the hook surface 106 on the first strap 103 is pulled away from the loop surface 107 on the second strap 104.

Figure 5:
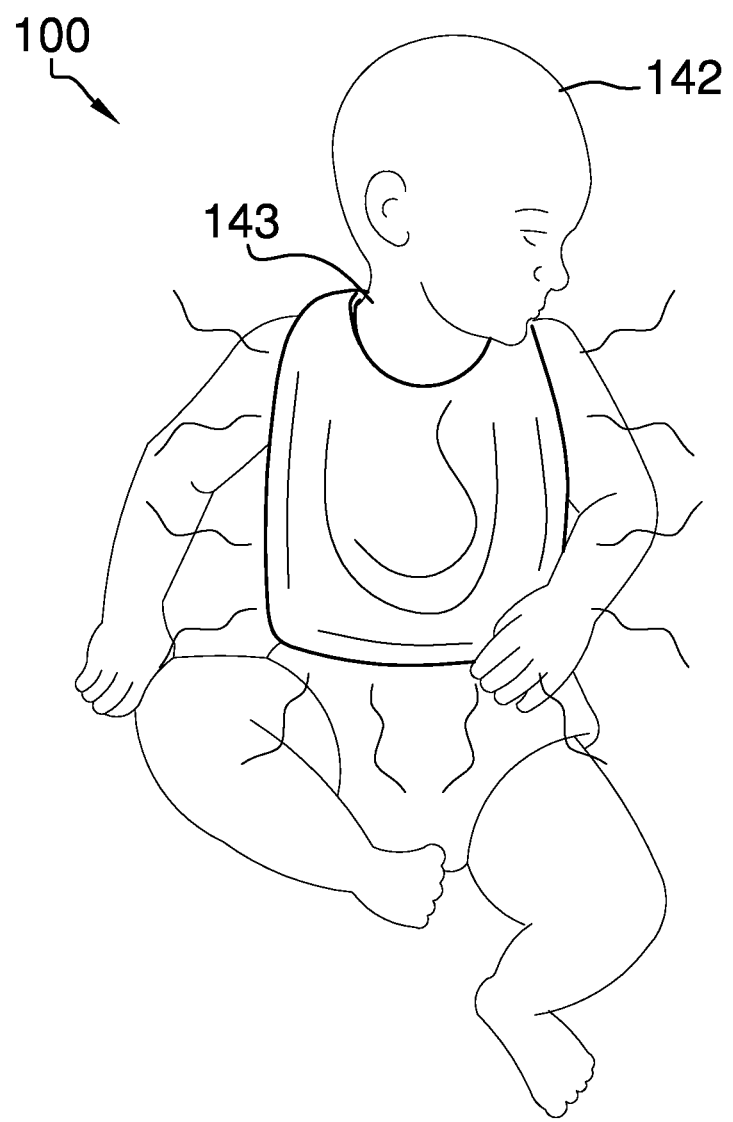
FIG. 5 is an in-use view of an embodiment of the disclosure.
Figure 6:
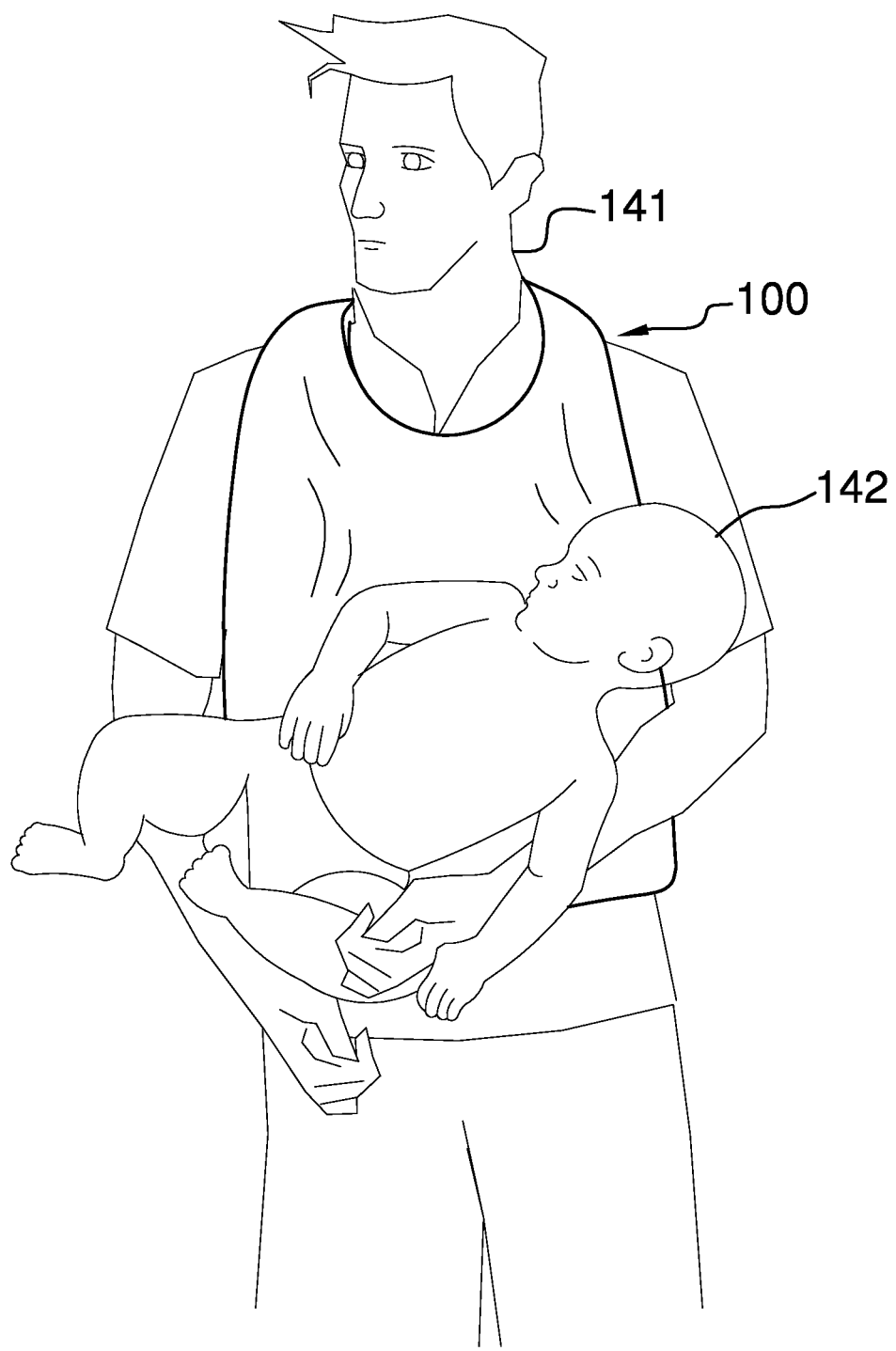
FIG. 6 is an embodiment of the disclosure in an alternative use.

In an alternate scenario, the bib 101 can be placed directly on the child 142 (see FIG. 5). In this alternate scenario, the cold pack 102 is thoroughly chilled and placed in the pocket 109. The invention 100 is secured by bringing the first strap 103 and the second strap 104 around the neck 143 of the child 142 and then pressing the hook surface 106 on the first strap 103 against the loop surface 107 on the second strap 104. In the alternate scenario, the cold pack 102 is used to draw heat away from the child 142. To remove the invention 100, the hook surface 106 on the first strap 103 is pulled away from the loop surface 107 on the second strap 104.

The following definitions were used in this disclosure:

Hook and Loop Fastener: As used in this disclosure, a hook and loop faster 105 is a fastener that comprises a hook surface 106 and a loop surface 107. The hook surface 106 comprises a plurality of minute hooks. The loop surface 107 comprises a surface of uncut pile that acts like a plurality of loops. When the hook surface 106 is applied to the loop surface 107, the plurality of minute hooks fasten to the plurality of loops securely fastening the hook surface 106 to the loop surface 107.

Textile: As used in this disclosure, a textile is a material that is woven, knitted or felted. Synonyms in common usage for this definition of textile include fabric and cloth.

Sheeting: As used in this disclosure, sheeting is a material, such as cloth or plastic, in the form of a thin flexible layer or layers that is used to cover something.

With respect to the above description, it is to be realized that the optimum dimensional relationship for the various components of the invention described above and in FIGS. 1 through 5, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

Is shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A child's bib for relieving a fever comprising:
a bib and a cold pack;
wherein the bib is adapted for use with a child;
wherein the bib receives the cold pack;
wherein the bib is adapted for use in relieving a fever of said child;
wherein the bib comprises a first strap, a second strap, a hook and loop fastener, a body, and a pocket;
wherein the hook and loop fastener further comprises a hook surface and a loop surface;
wherein the body, the first strap, and the second strap are formed from textile or sheeting;
wherein the textile or sheeting is nylon or plastic;
wherein the first strap and the second strap are attached to the body;
wherein the first strap and the second strap are adapted to be wrapped around the neck of said child or a caretaker whom is holding said child;
wherein the first strap and the second strap are secured using the hook and loop fastener;
wherein the hook surface is attached to the first strap by stitching or glue;
wherein the loop surface is attached to the second strap by stitching or glue;
wherein the bib has a curved depression formed between the first strap and the second strap to accommodate the neck of said child or said caretaker;
wherein the pocket is a rectangular shaped textile or sheeting;
wherein the pocket creates a pouch;
wherein the pocket is further defined by a first edge, a second edge, a third edge and a fourth edge;
wherein the first edge is attached to the body;
wherein the second edge is attached to the body;
wherein the third edge is attached to the body;
wherein at least one of the first, second or third edge is attached to the body by glue;
wherein a closing device is attached to the fourth edge and the body;
wherein the closing device is a zipper or button;
wherein the cold pack further comprises an alcohol solution and a vacuum sealed pouch;
wherein the alcohol solution is a 30% (v/v) solution of 2-propanol in water;
wherein the alcohol solution is stored in the vacuum sealed pouch;
wherein the child's bib is adaptively secured by bringing the first strap and the second strap around the neck of said child or said caretaker and pressing the hook surface on the first strap against the loop surface on the second strap; and
wherein the pocket is adapted to be held against the child.

* * * * *